US010292617B2

(12) United States Patent
Rapoport et al.

(10) Patent No.: US 10,292,617 B2
(45) Date of Patent: *May 21, 2019

(54) AUTOMATED TUNING AND FREQUENCY MATCHING WITH MOTOR MOVEMENT OF RF COIL IN A MAGNETIC RESONANCE LABORATORY ANIMAL HANDLING SYSTEM

(71) Applicant: Aspect Imaging Ltd., Shoham (IL)

(72) Inventors: Uri Rapoport, Moshav Ben Shemen (IL); Itzhak Rabinovitz, Nes Ziona (IL)

(73) Assignee: ASPECT IMAGING LTD., Shoham (IL)

( * ) Notice: Subject to any disclaimer, the term of this patent is extended or adjusted under 35 U.S.C. 154(b) by 1056 days.

This patent is subject to a terminal disclaimer.

(21) Appl. No.: 14/588,741

(22) Filed: Jan. 2, 2015

(65) Prior Publication Data

US 2015/0201862 A1 Jul. 23, 2015

Related U.S. Application Data

(60) Continuation-in-part of application No. 14/182,766, filed on Feb. 18, 2014, now Pat. No. 9,681,822, which
(Continued)

(51) Int. Cl.
*A61B 5/055* (2006.01)
*G01R 33/30* (2006.01)
(Continued)

(52) U.S. Cl.
CPC .......... *A61B 5/0555* (2013.01); *A01K 29/005* (2013.01); *A61D 3/00* (2013.01);
(Continued)

(58) Field of Classification Search
USPC .................. 324/300–322; 600/407–435; 382/128–131
See application file for complete search history.

(56) References Cited

U.S. PATENT DOCUMENTS 2,845,595 A * 7/1958 Leete .................. G01R 15/148
318/650
2,916,690 A * 12/1959 Leete ..................... G01R 33/24
324/301
(Continued)

FOREIGN PATENT DOCUMENTS

WO WO01/60076 8/2001
WO WO2006/020896 2/2006
(Continued)

OTHER PUBLICATIONS

Aspect Imaging Ltd., "Foamed Patient Transport Incubator", co-pending U.S. Appl. No. 14/531,289, filed Nov. 3, 2014.
(Continued)

*Primary Examiner* — Melissa J Koval
*Assistant Examiner* — Tiffany Fetzner
(74) *Attorney, Agent, or Firm* — Pearl Cohen Zedek Latzer Baratz LLP (57) ABSTRACT

An animal handling system for use in a magnetic resonance device (MRD) device, including: a first elongated enclosure having a proximal end, a distal open end and a first geometry, and a second elongated enclosure having a proximal end, a distal open end and a second geometry. The first geometry comprises a first cross-sectional area that is larger than a second cross-sectional area of the second geometry. The first elongated enclosure is inserted into a first input port of the MRD device and the second elongated enclosure is inserted in a second input port of the MRD device diametrically opposite to first input port. The first elongated enclosure and the second elongated enclosure are inserted into the
(Continued)

respective input ports, the second elongated enclosure slides into the first elongated enclosure through the open distal end of the first elongated enclosure.

13 Claims, 7 Drawing Sheets

Related U.S. Application Data is a division of application No. 13/241,367, filed on Sep. 23, 2011, now Pat. No. 8,807,084.

(60) Provisional application No. 61/387,992, filed on Sep. 30, 2010.

(51) Int. Cl.
　　*G01R 33/36*　　　(2006.01)
　　*A61D 3/00*　　　(2006.01)
　　*A01K 1/06*　　　(2006.01)
　　*A01K 29/00*　　　(2006.01)

(52) U.S. Cl.
　　CPC ............ *G01R 33/30* (2013.01); *G01R 33/36* (2013.01); *G01R 33/3628* (2013.01); *A61B 5/055* (2013.01); *A61B 2503/40* (2013.01)

(56) References Cited

U.S. PATENT DOCUMENTS

| | | | |
|---|---|---|---|
| 2,960,985 A | 11/1960 | Wiese, Jr. | |
| 3,367,632 A | 2/1968 | Vail | |
| 3,557,785 A | 1/1971 | McQueen | |
| 3,739,751 A | 6/1973 | Mohr et al. | |
| 3,907,389 A | 9/1975 | Cox et al. | |
| 3,986,480 A | 10/1976 | Vail | |
| 4,084,814 A | 4/1978 | Boggild | |
| 4,328,904 A | 5/1982 | Iverson | |
| 4,332,244 A | 6/1982 | Levy et al. | |
| 4,348,985 A | 9/1982 | Leong | |
| 4,520,808 A | 6/1985 | LaBauve | |
| 4,534,050 A | 8/1985 | Smith | |
| 4,633,890 A | 1/1987 | Carden | |
| 4,771,785 A | 9/1988 | Duer | |
| 4,875,485 A | 10/1989 | Matsutani | |
| 5,012,763 A | 5/1991 | Morrison | |
| 5,038,515 A | 8/1991 | Moorhead | |
| 5,066,915 A | 11/1991 | Omori et al. | |
| 5,085,219 A | 2/1992 | Ortendahl et al. | |
| 5,167,160 A | 12/1992 | Hall, II | |
| 5,194,041 A | 3/1993 | Trexler | |
| 5,331,920 A | 7/1994 | Coiro, Sr. et al. | |
| 5,490,513 A | 2/1996 | Damadian et al. | |
| 5,623,927 A | 4/1997 | Damadian et al. | |
| 5,676,133 A | 10/1997 | Hickle et al. | |
| 5,976,871 A | 11/1999 | Walker et al. | |
| 6,029,081 A | 2/2000 | Demeester et al. | |
| 6,137,291 A | 10/2000 | Szumowski et al. | |
| 6,317,618 B1 | 11/2001 | Livni et al. | |
| 6,352,076 B1 | 3/2002 | French | |
| 6,363,931 B1 | 4/2002 | Dellenbusch | |
| 6,609,325 B2 | 8/2003 | Harris | |
| 6,908,430 B2 | 6/2005 | Caldwell et al. | |
| 6,981,966 B2 | 1/2006 | Green et al. | |
| 7,037,254 B2 | 5/2006 | O'Connor et al. | |
| 7,113,217 B2 | 9/2006 | Nilson et al. | |
| 7,121,229 B2 | 10/2006 | Hong | |
| 7,222,587 B2 | 5/2007 | Hagel | |
| 7,345,483 B2 | 3/2008 | Vaughan | |
| 7,414,403 B2 | 8/2008 | Chiodo | |
| 7,680,525 B1 | 3/2010 | Damadian et al. | |
| 7,784,429 B2 | 8/2010 | Chiodo | |
| 7,789,820 B2 | 9/2010 | Akers et al. | |
| 7,865,226 B2 | 1/2011 | Chiodo | |
| 8,342,136 B2 | 1/2013 | Hadjioannou et al. | |
| 8,482,278 B2 | 7/2013 | Wolke et al. | |
| 8,660,633 B2 | 2/2014 | Zagorchev et al. | |
| 8,774,899 B2 | 7/2014 | Chiodo | |
| 8,807,084 B2 | 8/2014 | Rapoport et al. | |
| 8,851,018 B2 | 10/2014 | Rapoport et al. | |
| 8,854,042 B2 * | 10/2014 | Vaughan, Jr. ...... | G01R 33/3415 324/318 |
| 8,896,310 B2 | 11/2014 | Rapoport | |
| 8,918,163 B2 | 12/2014 | Yared et al. | |
| 9,655,542 B2 * | 5/2017 | Rapoport ............. | A61B 5/0555 |
| 9,770,188 B2 * | 9/2017 | Rapoport ............. | A61B 5/0555 |
| 9,995,803 B2 * | 6/2018 | Vaughan, Jr. ...... | G01R 33/3415 |
| 2001/0035181 A1 | 11/2001 | Elkins | |
| 2003/0011701 A1 | 1/2003 | Nilson et al. | |
| 2003/0195272 A1 | 10/2003 | Green et al. | |
| 2004/0116770 A1 | 6/2004 | O'Connor et al. | |
| 2004/0216737 A1 | 11/2004 | Anderson et al. | |
| 2005/0072719 A1 | 2/2005 | Chiodo | |
| 2005/0248349 A1 | 11/2005 | Okada et al. | |
| 2006/0074303 A1 | 4/2006 | Chornenky et al. | |
| 2006/0078195 A1 | 4/2006 | Vaillant et al. | |
| 2006/0145698 A1 | 7/2006 | Griffin | |
| 2006/0161050 A1 | 7/2006 | Butler et al. | |
| 2007/0238946 A1 | 10/2007 | Chiodo | |
| 2008/0072836 A1 | 3/2008 | Chiodo | |
| 2008/0085042 A1 | 4/2008 | Trofimov et al. | |
| 2008/0168948 A1 | 7/2008 | Truitt et al. | |
| 2009/0000567 A1 | 1/2009 | Hadjioannou et al. | |
| 2009/0010507 A1 | 1/2009 | Geng | |
| 2009/0056639 A1 | 3/2009 | Ragatz et al. | |
| 2009/0148012 A1 | 6/2009 | Altmann et al. | |
| 2010/0072999 A1 | 3/2010 | Wolke et al. | |
| 2010/0100072 A1 | 4/2010 | Chiodo | |
| 2010/0101500 A1 | 4/2010 | Sannie et al. | |
| 2010/0128953 A1 | 5/2010 | Ostrovsky-Berman | |
| 2010/0156414 A1 * | 6/2010 | Sakellariou ......... | G01R 33/307 324/309 |
| 2010/0198047 A1 | 8/2010 | Zagorchev et al. | |
| 2010/0269260 A1 | 10/2010 | Lanz et al. | |
| 2011/0071388 A1 | 3/2011 | Yared et al. | |
| 2011/0162652 A1 | 3/2011 | Rapoport | |
| 2011/0186049 A1 | 3/2011 | Rapoport | |
| 2011/0092807 A1 | 4/2011 | Chiodo | |
| 2011/0234347 A1 | 9/2011 | Rapoport | |
| 2011/0304333 A1 | 12/2011 | Rapoport | |
| 2012/0032678 A1 * | 2/2012 | Vaughan, Jr. ...... | G01R 33/3415 324/318 |
| 2012/0071745 A1 | 3/2012 | Rapoport | |
| 2012/0073509 A1 | 3/2012 | Rapoport et al. | |
| 2012/0073511 A1 | 3/2012 | Rapoport et al. | |
| 2012/0077707 A1 | 3/2012 | Rapoport | |
| 2012/0078088 A1 | 3/2012 | Whitestone et al. | |
| 2012/0083685 A1 * | 4/2012 | Rapoport ............... | G01R 33/30 600/410 |
| 2012/0119742 A1 | 5/2012 | Rapoport | |
| 2012/0155734 A1 | 6/2012 | Barratt et al. | |
| 2012/0223715 A1 | 9/2012 | Park et al. | |
| 2012/0278990 A1 | 11/2012 | Lanz et al. | |
| 2012/0330130 A1 | 12/2012 | Lanz et al. | |
| 2013/0061812 A1 | 3/2013 | Chiodo | |
| 2013/0079624 A1 | 3/2013 | Rapoport | |
| 2013/0109956 A1 | 5/2013 | Rapoport | |
| 2013/0237803 A1 | 5/2013 | Rapoport | |
| 2013/0193974 A1 | 8/2013 | McBroom et al. | |
| 2013/0234710 A1 | 9/2013 | Kanno et al. | |
| 2013/0293232 A1 | 11/2013 | Boskamp et al. | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport | |
| 2014/0103927 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |

(56) References Cited

U.S. PATENT DOCUMENTS

| | | |
|---|---|---|
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0378821 A1 | 12/2014 | Rapoport et al. |
| 2014/0378825 A1 | 12/2014 | Rapoport et al. |
| 2015/0059157 A1 | 3/2015 | Rapoport |
| 2015/0059655 A1 | 3/2015 | Rapoport |
| 2015/0065788 A1 | 3/2015 | Rapoport |
| 2015/0073204 A1 | 3/2015 | Rapoport |
| 2015/0077105 A1 | 3/2015 | Rapoport et al. |
| 2015/0087051 A1 | 3/2015 | Rapoport |
| 2015/0112186 A1* | 4/2015 | Rapoport ............ A61B 5/0555 600/415 |
| 2015/0123657 A1 | 5/2015 | Rapoport |
| 2015/0123660 A1* | 5/2015 | Vaughan, Jr. ...... G01R 33/3415 324/314 |
| 2015/0126804 A1 | 5/2015 | Rapoport |
| 2015/0137812 A1 | 5/2015 | Rapoport |
| 2015/0141799 A1 | 5/2015 | Rapoport et al. |
| 2015/0160311 A1 | 6/2015 | Rapoport et al. |
| 2015/0168519 A1 | 6/2015 | Rapoport |
| 2015/0201862 A1* | 7/2015 | Rapoport ............ A61B 5/0555 600/415 |
| 2015/0208994 A1 | 7/2015 | Rapoport |
| 2015/0212172 A1 | 7/2015 | Rapoport |
| 2015/0212173 A1 | 7/2015 | Rapoport |
| 2015/0231012 A1 | 8/2015 | Rapoport |
| 2015/0253397 A1 | 9/2015 | Rapoport |
| 2015/0253400 A1 | 9/2015 | Rapoport |
| 2015/0253401 A1 | 9/2015 | Rapoport |
| 2016/0077171 A1 | 3/2016 | Rabinovitz et al. |
| 2016/0077176 A1 | 3/2016 | Rabinovitz et al. |
| 2017/0086706 A1* | 3/2017 | Rapoport ............ A61B 5/0555 |

FOREIGN PATENT DOCUMENTS

| | | |
|---|---|---|
| WO | WO2008/084438 | 7/2008 |
| WO | WO2010/029547 | 3/2010 |

OTHER PUBLICATIONS

Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Aspect Imaging Ltd., "Shutting Assembly for Closing an Entrance of an MRI Device", co-pending U.S. Appl. No. 14/540,163, filed Nov. 13, 2014.
Aspect Imaging Ltd, "MRI-Incubator's Closure Assembly", co-pending U.S. Appl. No. 14/539,442, filed Nov. 12, 2014.
Aspect Imaging Ltd., "Cage in an MRD with a Fastening/Attenuating System", co-pending U.S. Appl. No. 14/527,950, filed Oct. 30, 2014.
Rapoport, Uri, "RF Shielding Conduit in an MRI Closure Assembly", co-pending U.S. Appl. No. 14/574,785, filed Dec. 18, 2014.
Aspect Imaging Ltd., "System and Method for Generating Invasively Hyperpolarized Images", co-pending U.S. Appl. No. 14/556,682, filed Dec. 1, 2014.
Aspect Imaging Ltd., "System and Method for Generating Invasively Hyperpolarized Images", co-pending U.S. Appl. No. 14/556,654, filed Dec. 1, 2014.
Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014
Aspect Imaging Ltd., "Chamber for Housing Animals During Anaesthetic Procedures", co-pending U.S. Appl. No. 14/537,266, filed Nov. 10, 2014.
Aspect Imaging Ltd., "RF Automated Tuning System Used in a Magnetic Resonance Device and Methods.Thereof", co-pending U.S. Appl. No. 14/588,741, filed Jan. 2, 2015.
Aspect Imaging Ltd., "Means for Operating an MRI Device Within a RF-Magnetic Environment", co-pending U.S. Appl. No. 14/596,320, filed Jan. 14, 2015.
Aspect Imaging Ltd., "Means and Method for Operating an MRI Device Within a RF-Magnetic Environment", co-pending U.S. Appl. No. 14/596,329, filed Jan. 14, 2015.
Aspect Imaging Ltd., "CT/MRI Integrated System for the Diagnosis of Acute Strokes and Methods Thereof", co-pending U.S. Appl. No. 14/598,517, filed Jan. 16, 2015.
X.Josette Chen: "Mouse Morphological Phenotyping With Magnetic Resonance Imaging", Methods in Molecular Medicine, vol. 124, 2006, pp. 103-127, XP009155743.
Aspect Magnet Technologies: "Aspect Imaging Products (Technical Features) and Press Releases (Aspect Magnet Technologies Delivers Multiple New Compact MRI Systems)", , Aug. 31, 2010 (Aug. 31, 2010), XP002667774, Retrieved from the Internet: URL:http://www.aspectimaging.com/ [retrieved on Jan. 24, 2012].
P.J.Cassidy et al.: "An Animal Handling System for Small Animal in vivo MR", Proc.Intl.Soc.Mag.Reson.Med. 13,2005. p. 2541, XP002667775.
European Serach Report for EP applicatoin No. 11182715 dated Feb. 2, 2012.
Office Action for U.S. Appl. No. 14/182,766 dated Sep. 9, 2016.
Office Action for U.S. Appl. No. 14/182,766 dated Feb. 2, 2016.
Handler, William, Simulation of scattering and attenuation of 511 keV photons in a combined PET/field-cycled MRI system; Simulation of scattering and attenuation of 511 keV photons, Physics in Medicine and Biology, Institute of Physics Publishing, May 21, 2006, vol. 51, No. 10, pp. 2479-2491.
MR-Technology Information Portal, retrieved at http://www.mt-tip.com, Sep. 23, 2011.
Aspect Imaging Ltd., "Method for Providing High Resolution, High Contrast Fused MRI Images", co-pending U.S. Appl. No. 13/877,553, filed Apr. 3, 2013.
Aspect Imaging Ltd., "Method for Manipulating the MRI's Protocol of Pulse Sequences", co-pending U.S. Appl. No. 14/070,695, filed Nov. 4, 2013.

* cited by examiner

AUTOMATED TUNING AND FREQUENCY MATCHING WITH MOTOR MOVEMENT OF RF COIL IN A MAGNETIC RESONANCE LABORATORY ANIMAL HANDLING SYSTEM

CROSS-REFERENCE TO RELATED APPLICATIONS

This application is a continuation-in-part application of U.S. patent application Ser. No. 14/182,766, filed Feb. 18, 2017, now U.S. Pat. No. 9,681,822, issued Jun. 20, 2017, divisional application of U.S. patent application Ser. No. 13/241,367, filed Sep. 23, 2011, now U.S. Pat. No. 8,807, 084, issued Aug. 19, 2014, which in turn claims priority from U.S. Provisional Patent Application No. 61/387,992, filed Sep. 30, 2010, all of which are incorporated herein by reference in their entirety.

FIELD OF THE INVENTION

The present invention generally pertains to an RF tuning systems for use in an MRI device; more specifically, the present invention relates to means and methods for automated tuning of the frequency of the RF magnetic field.

BACKGROUND OF THE INVENTION

Magnetic resonance imaging (MRI), or nuclear magnetic resonance imaging (NMRI), is primarily a noninvasive medical imaging technique used in radiology to visualize detailed internal structure and limited function of the body. MRI and NMRI devices are examples of a class of devices called magnetic response devices (MRD).

Objects to be analyzed are positioned within an MRI device in a predefined specific location and configuration. It is advantageous to adjust the location of the animal under inspection within the MRI device to obtain optimal analysis. Few patents pertain to means and methods of positioning analyzed objects. Hence for example, U.S. Pat. No. 5,066, 915 discloses an RF coil positioning device tier an MRI device in which a pallet is movably mounted on a mount and is moved by a drive means so that an RF coil unit mounted on the pallet is moved from its initial position at an imaging position in a magnetostatic field generator. Likewise, US patent discloses a diagnostic table for a medical imaging apparatus. However, the MRI operator in those MRI systems cannot routinely, quickly and easily switch between one object to another, and between one type of object to other object.

Fine tuning of the various shape, size and type objects, especially in laboratory routine, wherein a frequent switching of scanned objects of different type shape and size is practically impossible utilizing those MRI systems. In addition, the magnetic field produced by the MRI magnets is sensitive to variability of the magnets originally occurring in the manufacturing process. It is also sensitive to the ambient temperature of the examination area. Therefore, the frequency of the magnetic field changes between one venue and another, and between one operation and the next, and even once in every few scanning procedures. Radiofrequency transmitted by the RF coil assembly needs to match the main magnetic field in order to receive a clear signal, low noise and sharper images. The variability in the magnetic field can be compensated by tuning the frequency of the electromagnetic radiation transmitted by the RF coils. However, tuning of the RF coils is currently done manually by mechanically adjusting the location of the RF coils with respect to the magnetic field, and thus causing a change in the RF field. Such manual systems involve trial and error and are prone to elaborate and lengthy calibrations.

None of the above provides a simple solution for routine insertion of more than one maneuverable small and tangible objects, such as laboratory items (microplates laboratory animals etc), within a single lab-scale experimental MRI device. Hence an MRI device with a plurality of individually controllable entry ports and MRI-compatible inserts therefor fulfill a long felt need. Moreover, introducing an automated RF coil tuning system to the RF coil animal holding system, provided to automatically match the induced RF field to the main magnetic field, would also fulfill a long felt need.

SUMMARY OF THE INVENTION

It is thus one object of the present invention to provide in an MRD comprising a first input port and a second input port, and at least one magnetic source adapted to provide the MRD with a main effective magnetic field having frequency $M_M$; an animal handling system comprising: a first elongated enclosure having a first cross-sectional area; a second elongated enclosure having a second cross-sectional area smaller than the first cross-sectional area; the first elongated enclosure is insertable into the MRD's first input port; the second elongated enclosure is insertable into the MRD's second input port; and the second elongated enclosure is slideably insertable into the first elongated enclosure; at least one RF coil configured to provide the MRD with an RF magnetic field having frequency $M_{RF}$; and an automated RF tuning system comprising a motor and a computer readable medium configured to perform the following steps: measuring the frequency $M_M$ of the main magnetic field; measuring the frequency $M_{RF}$ of the RF magnetic field; comparing the frequency $M_M$ and the frequency $M_{RF}$; and aligning the $M_M$ with the $M_{RF}$, in a manner that if the $M_M$ and the $M_{RF}$ are substantially different, operating the motor by means of the computer readable medium to relocate the at least one RF coil thereby tuning the RF magnetic frequency $M_{RF}$ to align with the main magnetic frequency $M_M$.

It is also an object of the present invention to provide the abovementioned animal handling system wherein the motor is a DC step motor.

It is also an object of the present invention to provide the abovementioned animal handling system wherein the computer readable program is a console operable in a manner selected from the group consisting of automatic manner, semiautomatic manner and any combination thereof.

It is also an object of the present invention to provide the abovementioned animal handling system wherein at least one of the following is being held true: (a) the automated RF tuning system is adapted to align the main magnetic frequency $M_M$ with the RF magnetic frequency $M_{RF}$ in an average time of 30 seconds and in no longer than 120 seconds; (b) the automated RF tuning system is adapted to align the main magnetic frequency $M_M$ with the RF magnetic frequency $M_{RF}$ in an average of 2 iterations and in no more than 5 iterations.

It is also an object of the present invention to provide the abovementioned animal handling system wherein the automated RF tuning system is configured to automatically operate in predetermined time intervals.

It is also an object of the present invention to provide the abovementioned animal handling system further comprising visual means for visually indicating a current operation carried by the automated RF tuning system.

It is also an object of the present invention to provide the abovementioned animal handling system further comprising audio means for voicing a sound when at least one of the following is being held true: (a) the main magnetic frequency $M_M$ is aligned with the RF magnetic frequency $M_{RF}$; (b) a predetermined number of iterations is exceeded; or (c) a predetermined period of time is exceeded.

It is also an object of the present invention to provide the abovementioned animal handling system wherein the first elongated enclosure comprises at least two portions and the at least two portions are telescopic.

It is also an object of the present invention to provide the abovementioned animal handling system wherein the second elongated enclosure is configured for insertion of an experimental animal selected from the group consisting of a rodent, a cat, a dog, a rabbit and laboratory experimental animals.

It is also an object of the present invention to provide the abovementioned animal handling system wherein the first elongated enclosure comprises a reaction testing device.

It is another object of the present invention to provide a method for tuning RF frequency provided in an animal handling system used in an MRD device, the method comprising steps as follows: providing an MRD with a first input port and a second input port; generating within the MRD a main magnetic field having frequency $M_M$, by at least one magnetic source; generating within the MRD an RF magnetic field having frequency $M_{RF}$, by at least one RF coil; providing an animal handling system having a first elongated enclosure with a first cross-sectional area; a second elongated enclosure with a second cross-sectional area smaller than the first cross-sectional area; inserting the first elongated enclosure into a first input port of the MRD device, inserting the second elongated enclosure into a second input port of the MRD device, and slideably inserting the second elongated enclosure into the first elongated enclosure, thereby generating a sealed experimental enclosure; providing the animal handling system with an automated RF tuning system comprising a computer readable medium and a motor; measuring the frequency $M_M$ of the main magnetic field; measuring the frequency $M_{RF}$ of the RF magnetic field; comparing the frequency $M_M$ and the frequency $M_{RF}$; and if substantially different, relocating the at least one RF coil by the motor, thereby tuning the RF magnetic frequency $M_{RF}$ to align with the main magnetic frequency $M_M$.

It is also an object of the present invention to provide the aforementioned method wherein relocating the at least one RF coil by the motor is provided automatically or semi-automatically by a console.

It is also an object of the present invention to provide the aforementioned method wherein at least one of the following is held true: (a) the aligning the main magnetic frequency $M_M$ with the RF magnetic frequency $M_{RF}$ is provided in an average time of 30 seconds and in no longer than 120 seconds; (b) the aligning the main magnetic frequency $M_M$ with the RF magnetic frequency $M_{RF}$ is provided in an average of 2 iterations and in no more than 5 iterations.

It is also an object of the present invention to provide the aforementioned method further comprising visually indicating a current operation carried by the automated RF tuning system.

It is also an object of the present invention to provide the aforementioned method further comprising voicing a sound when at least one of the following is being held true: (a) the main magnetic frequency $M_M$ is aligned with the RF magnetic frequency $M_{RF}$; (b) a predetermined number of iterations is exceeded; or (c) a predetermined period of time is exceeded.

It is another object of the present invention to provide an RF tuning system for use in an MRD, the MRD comprises: a first input port and a second input port; at least one magnetic source adapted to provide the MRD with a main magnetic field characterized by magnetic frequency $M_M$; and at least one RF coil adapted to provide the MRD with an RF magnetic field characterized by magnetic frequency $M_{RF}$; and the automated RF tuning system comprises a computer readable medium and a motor; wherein the computer readable medium is adapted to perform the following: measure the frequency $M_M$ of the main magnetic field; measure the frequency $M_{RF}$ of the RF magnetic field; compare the frequency $M_M$ and the frequency $M_{RF}$; and align the $M_M$ with the $M_{RF}$, such that if the $M_M$ and the $M_{RF}$ are substantially different, the computer readable medium is configured to operate the motor to relocate the at least one RF coil so as to align the main magnetic frequency $M_M$ with the RF magnetic frequency $M_{RF}$.

It is also an object of the present invention to provide the aforementioned RF tuning system wherein the motor is a DC step motor.

It is also an object of the present invention to provide the aforementioned RF tuning system wherein the computer readable program is a console operable in a manner selected from the group consisting of automatic manner, semiautomatic manner and any combination thereof.

It is also an object of the present invention to provide the aforementioned RF tuning system wherein at least one of the following is being held true: (a) the automated RF tuning system is adapted to align the main magnetic frequency $M_M$ with the RF magnetic frequency $M_{RF}$ in an average time of 30 seconds and in no longer than 120 seconds; (b) the automated RF tuning system is adapted to align the main magnetic frequency $M_M$ with the RF magnetic frequency $M_{RF}$ in an average of 2 iterations and in no more than 5 iterations.

It is also an object of the present invention to provide the aforementioned RF tuning system wherein at least one of the following is being held true: (a) the automated RF tuning system is configured to automatically operate in predetermined time intervals; (b) the RF tuning system further comprises visual means for visually indicating a current operation carried by the automated RF tuning system; or (c) the RF tuning system further comprises audio means for voicing a sound when at least one of the following is being held true: (a) the main magnetic frequency $M_M$ is aligned with the RF magnetic frequency $M_{RF}$; (b) a predetermined number of iterations is exceeded; or (c) a predetermined period of time is exceeded.

It is another object of the present invention to provide a method for tuning RF frequency provided in an MRD device, the method comprising steps as follows: generating within the MRD a main magnetic field having frequency $M_M$, by at least one magnetic source; generating within the MRD an RF magnetic field having frequency $M_{RF}$, by at least one RF coil; providing the animal handling system with an automated RF tuning system comprising a computer readable medium and a motor; measuring the frequency $M_M$ of the main magnetic field; measuring the frequency $M_{RF}$ of the RF magnetic field; comparing the frequency $M_M$ and the frequency $M_{RF}$; and if substantially different, relocating the at least one RF coil by the motor, thereby tuning the RF magnetic frequency $M_{RF}$ to align with the main magnetic frequency $M_M$.

It is one more object of the present invention to provide a method for tuning RF frequency provided in an MRD device, the method comprising steps as follows: generating within the MRD a main magnetic field having frequency $M_M$, by at least one magnetic source; generating within the MRD an RF magnetic field having frequency $M_{RF}$, by at least one RF coil; providing the animal handling system with an automated RF tuning system comprising a motor; and relocating the at least one RF coil by the motor, thereby tuning the RF magnetic frequency $M_{RF}$ to align with the main magnetic frequency $M_M$.

It is yet another object of the present invention to provide in an MRD comprising a first input port and a second input port, and at least one magnetic source adapted to provide the MRD with a main effective magnetic field having frequency $M_M$; an animal handling system comprising: a first elongated enclosure having a first cross-sectional area; a second elongated enclosure having a second cross-sectional area smaller than the first cross-sectional area; the first elongated enclosure is insertable into the MRD's first input port; the second elongated enclosure is insertable into the MRD's second input port; and the second elongated enclosure is slideably insertable into the first elongated enclosure; at least one RF coil configured to provide the MRD with an RF magnetic field having frequency $M_{RF}$; and an automated RF tuning system comprising a motor configured to relocate the at least one RF coil thereby tuning the RF magnetic frequency $M_{RF}$ to align with the main magnetic frequency $M_M$.

It is another object of the present invention to provide a method for tuning RF frequency provided in an animal handling system used in an MRD device, the method comprising steps as follows: providing an MRD with a first input port and a second input port; generating within the MRD a main magnetic field having frequency $M_M$, by at least one magnetic source; generating within the MRD an RF magnetic field having frequency $M_{RF}$, by at least one RF coil; providing an animal handling system having a first elongated enclosure with a first cross-sectional area; a second elongated enclosure with a second cross-sectional area smaller than the first cross-sectional area; inserting the first elongated enclosure into a first input port of the MRD device, inserting the second elongated enclosure into a second input port of the MRD device, and slideably inserting the second elongated enclosure into the first elongated enclosure, thereby generating a sealed experimental enclosure; providing the animal handling system with an automated RF tuning system comprising a motor; and relocating the at least one RF coil by the motor, thereby tuning the RF magnetic frequency $M_{RF}$ to align with the main magnetic frequency $M_M$.

It is another object of the present invention to provide an RF tuning system for use in an MRD, the MRD comprises: a first input port and a second input port; at least one magnetic source adapted to provide the MRD with a main magnetic field characterized by magnetic frequency $M_M$; and at least one RF coil adapted to provide the MRD with an RF magnetic field characterized by magnetic frequency $M_{RF}$; and the automated RF tuning system comprises a motor; wherein the motor is configured to relocate the at least one RF coil thereby tuning the RF magnetic frequency $M_{RF}$ to align with the main magnetic frequency $M_M$.

Further in accordance with a preferred embodiment of the present invention, the first cross-sectional area is less than the second cross-sectional area.

Still further in accordance with a preferred embodiment of the present invention the first cross-sectional is different from the second cross-sectional area.

There is provided in accordance with another (preferred embodiment of the present invention an animal handling system for use in an MRD device including: a first elongated enclosure having a proximal end, a distal open end and a first geometry, and a second first elongated enclosure having a proximal end, a distal open end and a second geometry. The second geometry includes a first cross-sectional area which is larger than a second cross-sectional area of the second geometry. The first elongated enclosure is inserted into a first input port of the MRD device and the second elongated enclosure is inserted in a second input port of the MRD device diametrically opposite to second input port, such that on insertion of the first elongated enclosure into the first input port and insertion of the second elongated enclosure into the second input, the second elongated enclosure slides into the first elongated enclosure through the open distal end of the first elongated enclosure.

Further in accordance with another preferred embodiment of the present invention the first elongated enclosure includes at least two portions the at least two portions are telescopic.

Still further in accordance with another preferred embodiment of the present invention the proximal end of the first elongated enclosure is sealed against a circumferential edge of the first input port and the proximal end of the second elongated enclosure is sealed against a circumferential edge of the second input port thereby sealing the first and second elongated enclosures from the outside environment.

Additionally in accordance with another preferred embodiment of the present invention a mammal for experimenting is inserted into the second elongated enclosure.

Furthermore in accordance with another preferred embodiment of the present invention the first elongated enclosure includes a reaction testing device.

Further in accordance with another preferred embodiment of the present invention the mammal is selected from the group consisting of a rodent, a cat, a dog, a rabbit and laboratory experimental animals.

BRIEF DESCRIPTION OF THE DRAWINGS

The novel features believed to be characteristics of the invention are set forth in the appended claims. The invention itself, however, as well as the preferred mode of use, further objects and advantages thereof, will best be understood by reference to the following detailed description of illustrative embodiment when read in conjunction with the accompanying drawings, wherein:

FIGS. 3A and 3B illustrate in an out-of-scale manner the assembly of the automated RF tuning system provided by the present invention; where FIGS. 3A and 3B illustrate a front view of the assembly, and a 3D perspective view of the assembly, respectively.

DETAILED DESCRIPTION OF THE PREFERRED EMBODIMENTS

The following description is provided in order to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for routine handling and scanning of items in a single MRD.

The term 'Magnetic Resonance Device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) spectroscope or any combination thereof. The MRD hereby disclosed is optionally a portable MRI device, such as devices commercially available from Aspect imaging (Toronto, Canada), or a commercially available non-portable device. Moreover, the term 'MRD' generally refers in this patent to any medical device configured to accommodate, at least temporarily, an anesthetized animal.

As used herein, the term "animal" or "mouse" refers interchangeably to any living creature, such as neonates, other mammals such as mice, rats, cats, dogs, rabbits etc., and laboratory animals.

As used herein, the term "object" generally refers to items to be scanned, and includes, in a non-limiting manner, laboratory items, such as microplates, microwells, tubes, veils, EPPENDORF tubes and the like, animals, organs, tissues, reaction solutions, cell media, organic or inorganic matter and compositions thereof, etc.

As used herein, the term "plurality" refers in a non-limiting manner to any integer equal to or greater than 1.

As used herein, the term "motor" generally refers to any kind of an electric motor, namely a machine converting electrical energy into mechanical energy.

As used herein, the term "console" generally refers to a system console, computer console or root console which is the physical device consisting of a keyboard and a screen and computer containing an operating system program.

As used herein, the term "computer readable medium" generally refers to any physical device used to store programs (sequences of instructions) or data (e.g. program state information) on a temporary or permanent basis for use in a computer or other digital electronic device.

The automated RF tuning system disclosed by the present invention recites some main principles; the tuning can be made by semiautomatic manner (i.e. manually operating the motor by controlling commands given by a user of a console) or in an automatic manner by a fully automatic operated by a console. The solution combines computer readable medium assembled on the MHS and which identifies the connected coil and stores information about several calibration parameters which are used during the auto-tuning (AT), together with firmware that supports communication with the console. The tuning takes place by mechanically adjusting through means of a motor the location or position of the RF coil assembly with respect to the main magnetic field.

Figure 1:
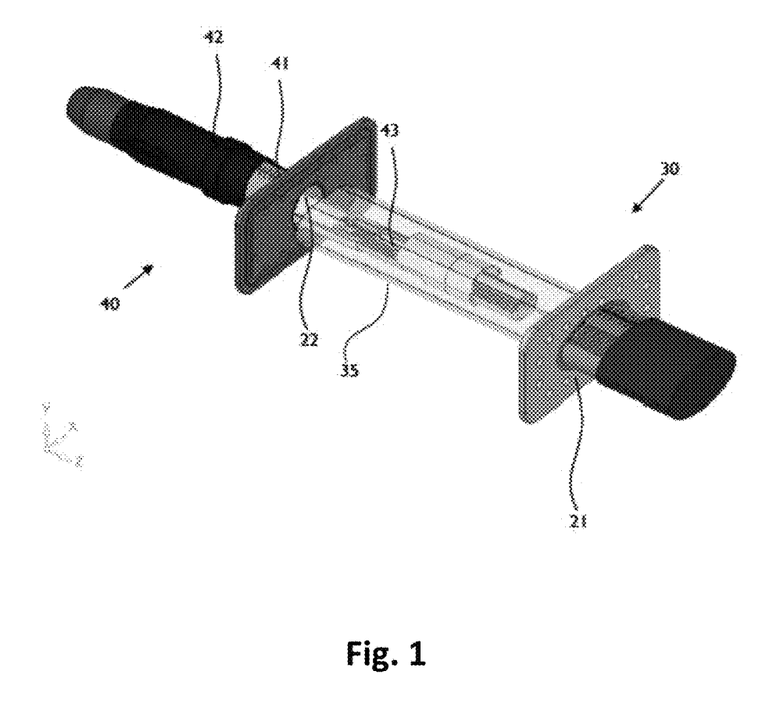
FIG. 1 illustrates two Mouse Handling Systems (MHS)

Reference is now made to FIG. 1, schematically illustrating in an out-of-scale manner both MHS 30 and MHS 40. FIG. 1 further shows that MHS 30 has an ellipsoidal cross-section and MHS 40 has a circular cross-section. Typically, the circular cross-sectional area of MHS 40 is less than the cross-sectional area of MHS 30. According to the illustrated embodiment of the invention, both MHS 30 and MHS 40 are maneuverable elongated devices. Each one of the MHSs is characterized by a proximal end portion, which is located outside of MRD 10 and possibly comprises an inserting abutment 41. At a distal end portion 43, the objects to be scanned are immobilized in a predefined configuration. The maneuverable MHSs 30 and 40 are rotatable about their respective main longitudinal axes and translatable parallel to shafts 35 and 43.

Figure 2:
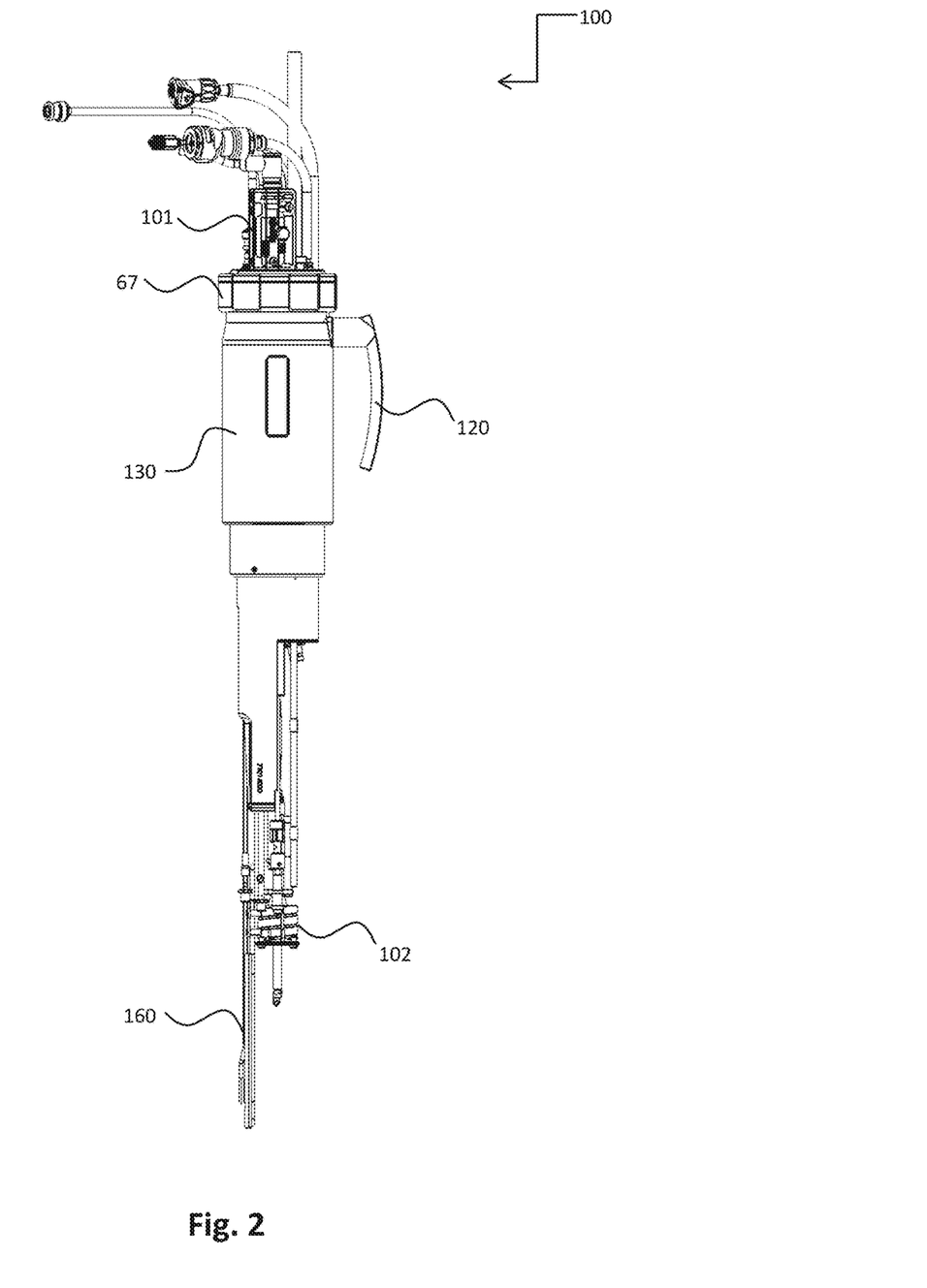
FIG. 2 illustrates in an out-of-scale manner an embodiment of the high level assembly comprising the automated RF tuning system in the MHS.

Reference is now made to FIG. 2, schematically illustrating in an out of scale manner the high level animal handling system 100 assembly comprising automated RF tuning electronics cage 101 and motor 102. FIG. 2 illustrates the front view of the assembly and the preferred embodiment having the tuning system positioned on the proximal portion of the MHS as disclosed by the present invention. RF tuning electronics cage 101 is preferably put together under an end cover (not shown) connected through its proximal end to tube press assembly 130 which contains the communication means of RF tuning electronics cage 101 with motor 102, along with other communication cords residing in the MHS. Tube press assembly 130 may be disconnected from the electronics cage by handle 120. Tube the press assembly 130 is configured to connect to the tuning assembly on its distal end and connect to the MHS on its proximal end. The connection may take place via a connector 67, which may be in a non-limiting example a nut connector, twist-on connector and/or an end ring. In some embodiments, the tuning system may further comprise a cable organizer, which may be connected to the distal end of the end cover.

In a preferred embodiment, information and data may be stored on a computer readable medium, pertaining to calibration related parameters, including the RF coil serial number, the RF coil type in a decimal value, the RF coil name in ASCII text, a decimal value parameter for coil motor calibration, tuning range frequency limits and any other RF related parameters.

In an embodiment, the automated RF tuning system may include a visual indicator such as one or more LEDs, to provide feedback to an operator as to the current working stage of the automated RF tuning system and whether the frequency $M_{RF}$ of the magnetic RF field transmitted by the RF coil is aligned with the frequency $M_M$ of the main magnetic field.

In another embodiment, the automated RF tuning system may also include audio means for voicing sounds in a scenario exhibiting the tuning system has finished aligning the magnetic field frequencies, or in case a predetermined number of iterations is exceeded, or a predetermined period of time is exceeded. An iteration is recited in the present invention as comprising the steps of measuring the frequency $M_M$ of the main magnetic field; measuring the frequency $M_{RF}$ of the RF magnetic field provided by the RF coils; comparing the frequencies and in case a misalignment is present, or the frequencies don't match to a certain extent, communicate to the motor the number of steps to take, in order to dislocate the RF coil and thus match its frequency to the main magnet's frequency. The number of iterations executed in the present invention leading to an alignment between the main magnetic frequency $M_M$ and the RF coil magnetic frequency $M_{RF}$ is on average 2, and preferably at a maximum of 5 such iterations. The total time required for reaching this alignment is on average 30 seconds, and preferably up to 120 seconds.

Figure 3A:
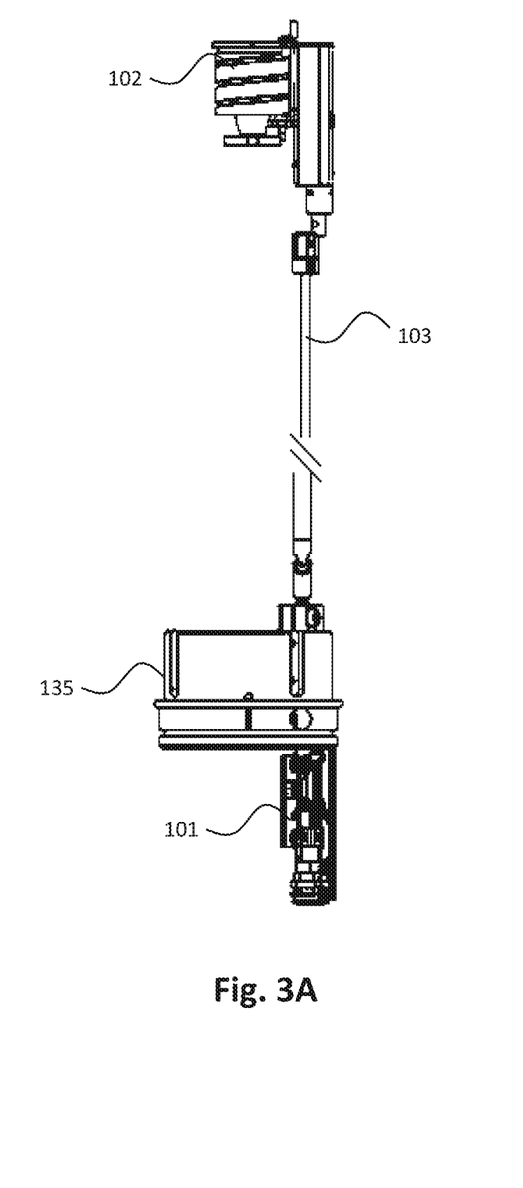
Figure 3B:
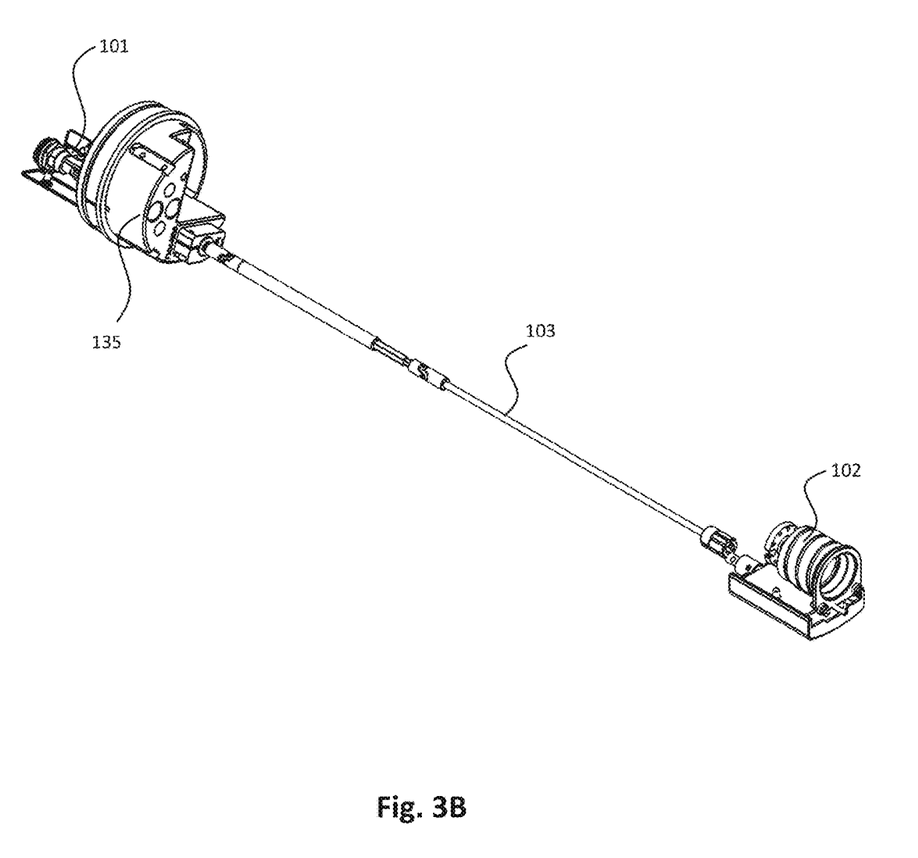

Reference is now made to FIGS. 3A and 3B, illustrating in an out-of-scale manner the assembly of the automated RF tuning system provided by the present invention; FIGS. 3A and 3B illustrate a front view of the assembly, and a 3D perspective view of the assembly, respectively. FIGS. 3A and 3B exemplifies RF tuning electronics cage 101, passing communication means 103 through system organizer 135, to communicate with motor 102, which is preferably a DC step motor and the communication means may be an electrical cord.

Figure 4:
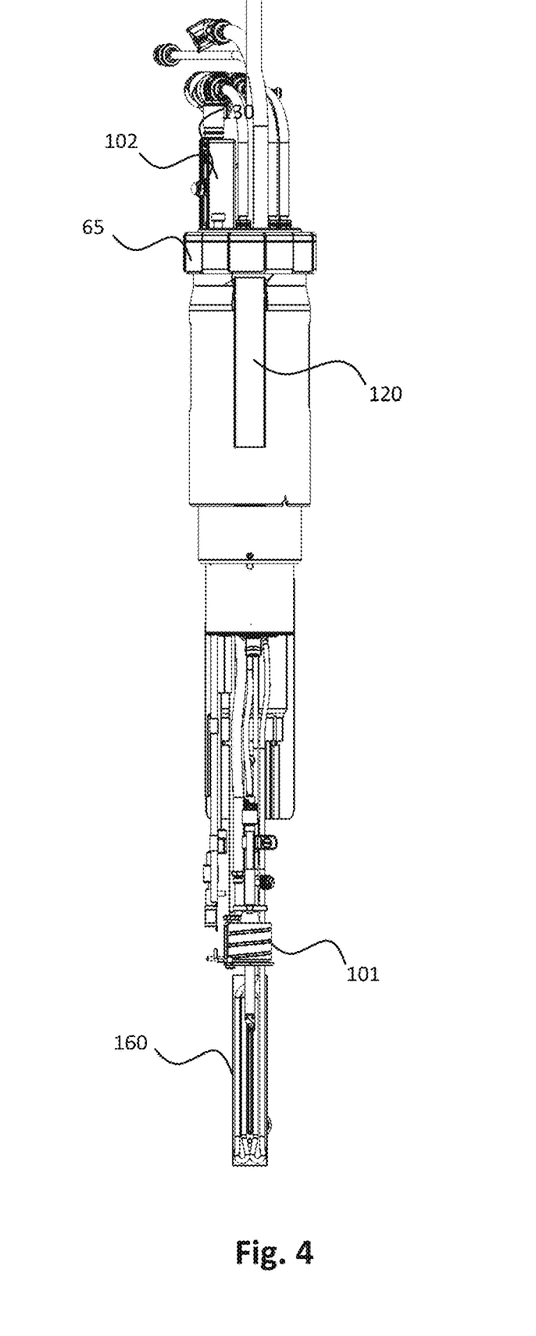
FIG. 4 illustrates a top view of the MHS comprising the automated RF tuning system and the RF coils.

Reference is now made to FIG. 4 illustrating a top view of MHS 100 assembly comprising the automated RF tuning system and the RF coils. The automated RF tuning system comprises electronics cage 101 and motor 102. The electronics cage is connected to the MHS through connector 65, which holds it together with tube assembly 130. Handle 120 is available to disconnect the MHS from the electronics cages. The motor is located in mechanical proximity to RF coil 160, and is configured to relocate RF coil 160 and thus change the frequency of the RF magnetic field transmitted by it.

Figure 5:
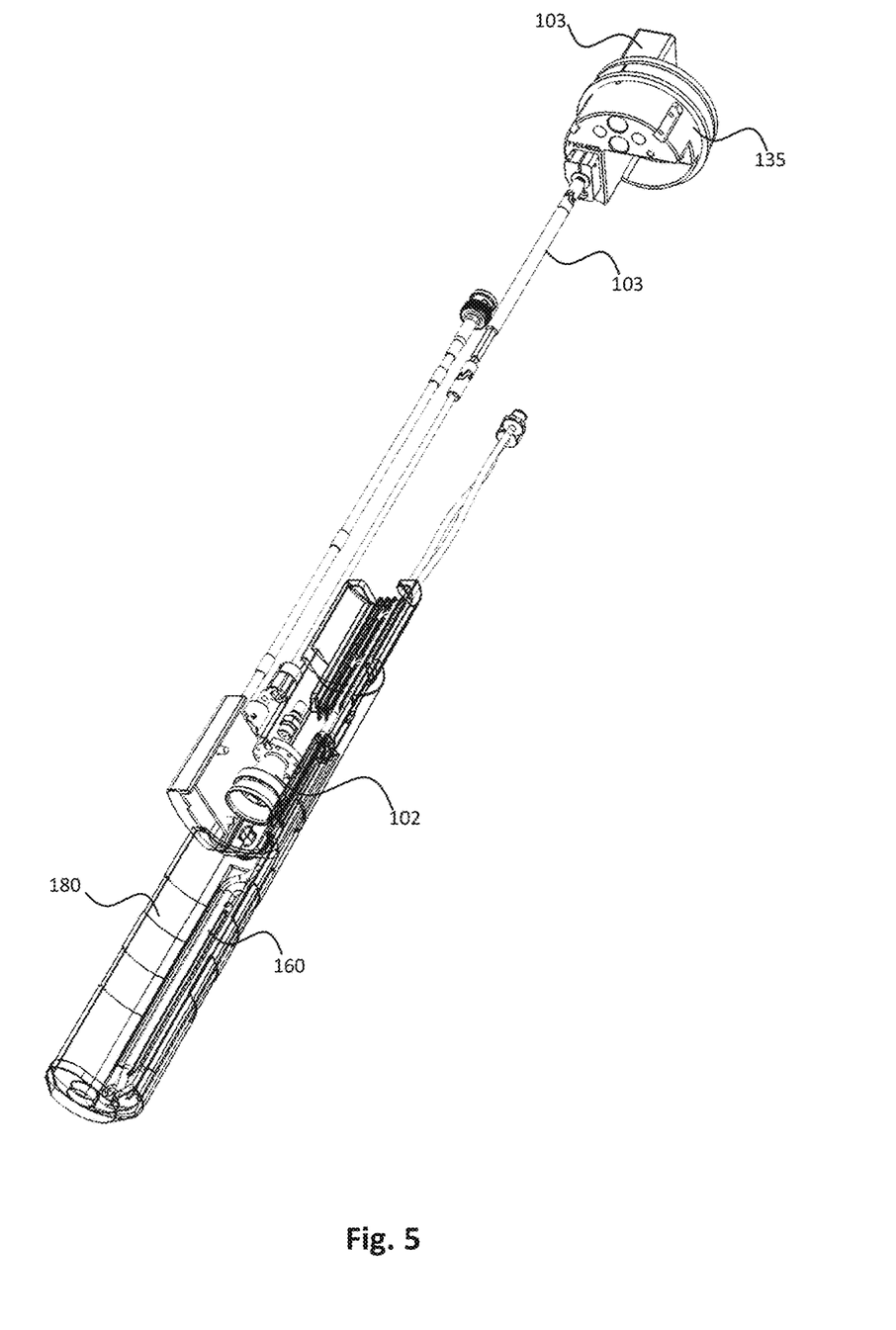
FIG. 5 illustrates a 3D perspective view of the MHS comprising the automated RF tuning system, the RF coils and the MHS bed.

Reference is now made to FIG. 5 illustrating a 3D perspective view of the MHS comprising the automated RF tuning system, including electronics cage 101, motor 102 and communication means 103, as well as RF coils 160, and further comprising MHS bed 180.

Figure 6:
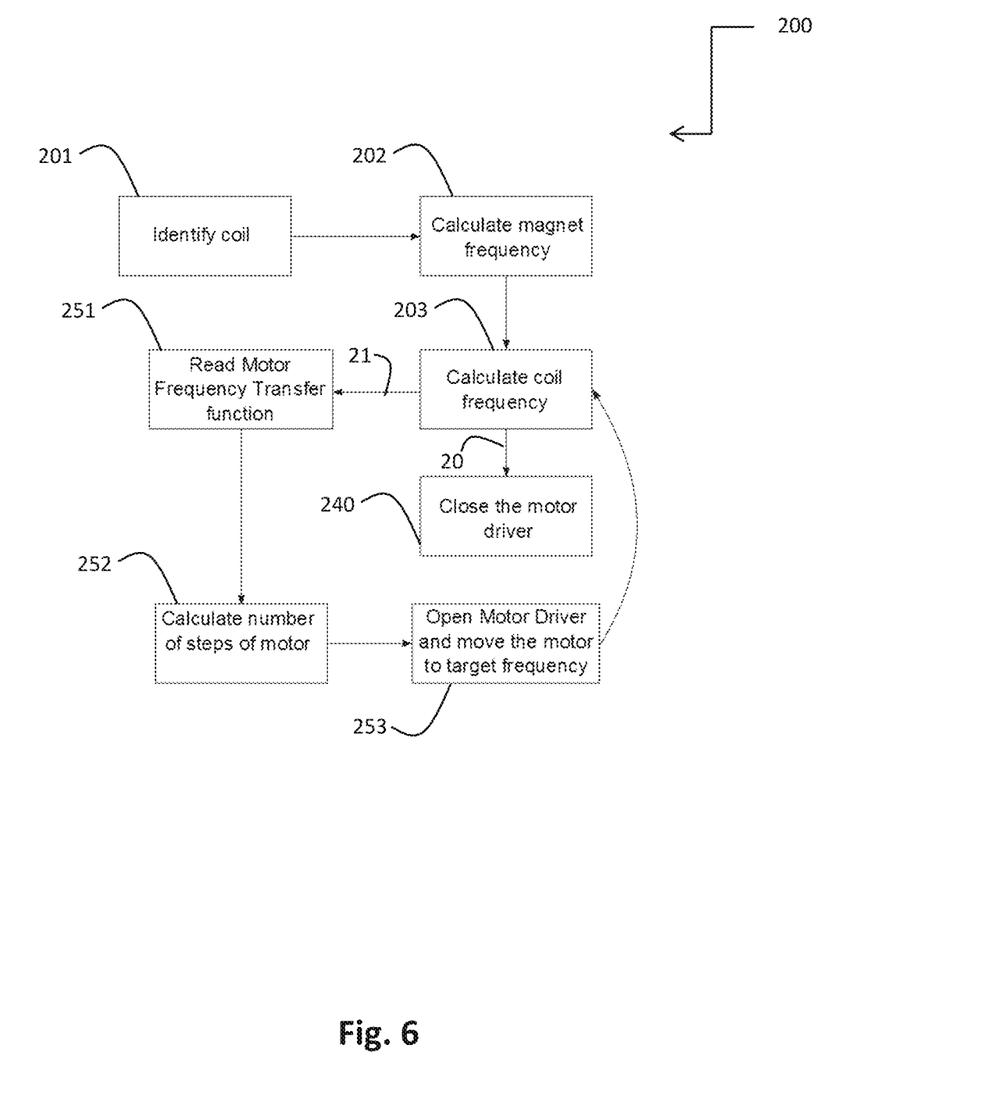
FIG. 6 illustrates the automatic tuning algorithm.

Reference is now made to FIG. 6 disclosing the automatic tuning algorithm 200 of the automated RF tuning system disclosed by the present invention. The algorithm starts by identifying the RF coil 201 through the computer readable medium comprised in the RF coil and containing coil calibration parameters. Next, the main magnetic field frequency $M_M$ is measured 202 and compared to the measured RF coil transmitted frequency $M_{RF}$ 240. If the frequencies match (i.e. align) 20, the algorithm shuts down the motor drive. However, if the frequencies do not match 21, then the algorithm proceeds to reading the Motor Frequency Transfer function 251, which assigns a conversion function for each identified RF coil for translating the desired frequency modulation into executable motor steps. The function is then used for calculating the number of steps the motor needs to execute 252, which is followed by opening the motor driver and operating the motor to relocate the RF coils, thus correct the RF frequency 253 to match the magnetic frequency. The algorithm then returns to step 203 of calculating the RF coil frequency and comparing it to the main magnetic field frequency.

The automatic tuning system provided by the present invention is employed in an MRD system. The MRD system is in operable communication with a console having a display, a keyboard and includes a processor that is a commercially available programmable machine running a commercially available operating system. The processor contains the coil calibration application which comprises instructions for tuning the RF frequency via the motor. The console and an electronic cage of the MRD system are connected to communicate with each other. The console provides the user an interface that enables automatic and/or semiautomatic commands to be transmitted into the electronic cage. The motor driver found in the MRD magnet functions in response to instructions transmitted from the console through the electronics cage to operate the motor residing in the animal handling system, which comprises the RF coil. The coil further comprises a computer readable medium 142 for storing coil identification information, calibration information and data.

In various embodiments, the console of the MRD may be operable by using a mouse, a keypad, touch screen, voice activated and such. The tuning system may also be remotely controlled.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. In a magnetic resonance device (MRD) comprising a first input port and a second input port, and at least one magnetic source configured to provide said MRD with a main effect of magnetic field having frequency $M_m$; and animal handling system comprising: a first elongated enclosure having a first cross-sectional area; said first elongated enclosure is insertable into said MRD's first input port; said second elongated enclosure is insertable into said MRD's second input port; and said second elongated enclosure is slidably insertable into said first elongated enclosure; at least one RF coil configured to provide said MRD with an RF magnetic field having frequency M RF; and an automated RF tooting system comprising a motor and a non-transitory computer readable medium configured to perform the following steps: measuring said frequency $M_M$ of said main magnetic field; measuring said frequency $M_{RF}$ of said RF magnetic field; comparing said frequency MM and said frequency $M_{RF}$; and aligning said $M_M$ and said $M_{RF}$, in a manner that when said $M_M$ and said $M_{RF}$ are substantially different, operating said motor by means of said non-transitory computer readable medium in order to relocate said at least one RF coil thereby tuning said RF magnetic frequency $M_{RF}$ in order to align with said main magnetic frequency $M_M$, wherein said motor is a DC stepper motor.

2. The animal handling system according to claim 1, wherein said non-transitory computer readable medium is a console operable in a manner selected from the group consisting of automatic manner, and semiautomatic manner.

3. The animal handling system according to claim 1, wherein at least one of the following is being held true: (a) said automated RF tooting system is configured to align said main magnetic frequency $M_M$ with said RF magnetic frequency $M_{RF}$ in an average time of 30 seconds and in no longer than 120 seconds; (b) said automated RF tooting system is configured to align said main magnetic frequency $M_M$ with said RF magnetic frequency $M_{RF}$ in an average of two iterations and in no more than five iterations.

4. The animal handling system according to claim 1, wherein said automated RF tuning system is configured to automatically operate in predetermined time intervals.

5. The animal handling system according to claim one, further comprising a visual means for visually indicating a current operation being carried out by said automated RF tuning system.

6. The animal handling system according to claim 1, further comprising audio means for voicing a sound when at least one of the following is being held true: (a) said main magnetic frequency $M_M$ is aligned with said RF magnetic frequency $M_{RF}$; (b) a predetermined number of iterations is exceeded; or (c) a predetermined period of time is exceeded.

7. The animal handling system according to claim 1, wherein said first elongated enclosure comprises at least two portions and said at least two portions are telescopic.

8. The animal handling system according to claim 1, wherein said second elongated enclosure is configured for insertion of an experimental animal selected from the group consisting of a rodent, a cat, a dog, a rabbit and laboratory experimental animals.

9. The animal handling system according to claim 8, wherein said first elongated enclosure comprises a reaction testing device.

10. An RF tuning system for use in a magnetic resonance device (MRD) comprises: a first input port and a second input port; at least one magnetic source configured to provide said MRD within RF magnetic field characterized by the magnetic frequency $M_{RF}$; and said automated RF tuning system comprising a non-transitory computer readable medium and a motor; wherein said non-transitory computer readable medium is configured to perform the following: measure said frequency $M_M$ of said main magnetic field; measure said frequency $M_{RF}$ of said RF magnetic field; compare said frequency $M_M$ and said frequency $M_{RF}$; and align said $M_M$ with said $M_{RF}$, such that when said $M_M$ and said $M_{RF}$ are substantially different, said non-transitory computer readable medium is configured to operate said motor in order to relocate said at least one RF coil so as to align said main magnetic frequency $M_M$ with said RF magnetic frequency $M_{RF}$, wherein said motor is a DC step motor.

11. The RF tuning system according to claim 10, wherein said non-transitory computer readable medium is a console operable in a manner selected from the group consisting of automatic manner, semiautomatic manner.

12. The RF tuning system according to claim 10, wherein at least one of the following is being held true: (a) said automated RF tooting system is configured to align said main magnetic frequency $M_M$ with said RF magnetic frequency $M_{RF}$ in an average time of 30 seconds and in no longer than 120 seconds; (b) said automated RF tooting system is configured to align said main magnetic frequency $M_M$ with said RF magnetic frequency $M_{RF}$ in an average of two iterations and in no more than five iterations.

13. The RF tuning system according to claim 10, wherein at least one of the following is being held true: (a) said automated RF tuning system is configured to automatically operate in predetermined time intervals; (b) said RF tuning system further comprises visual means for visually indicating a current operation carried by said automated RF tuning system; or (c) said RF tuning system further comprises audio means for voicing a sound when at least one of the following is being held true: (a) said main magnetic frequency $M_M$ is aligned with said RF magnetic frequency $M_{RF}$; (b) a predetermined number of iterations is exceeded; or (c) a predetermined period of time is exceeded.

* * * * *